US010821031B2

(12) United States Patent
Soli et al.

(10) Patent No.: US 10,821,031 B2
(45) Date of Patent: Nov. 3, 2020

(54) METHOD AND A MACHINE FOR MAKING ABSORBENT SANITARY ARTICLES

(71) Applicant: GDM S.p.A., Bologna (IT)

(72) Inventors: Valerio Soli, Bologna (IT); Matteo Piantoni, Albino (IT); Mauro Pietralunga, Crema (IT); Federico Tordini, Pedrengo (IT); Marco Rosani, Vailate (IT)

(73) Assignee: GDM S.P.A., Bologna (IT)

( * ) Notice: Subject to any disclaimer, the term of this patent is extended or adjusted under 35 U.S.C. 154(b) by 178 days.

(21) Appl. No.: 16/077,260

(22) PCT Filed: Jan. 30, 2017

(86) PCT No.: PCT/IB2017/050476
§ 371 (c)(1),
(2) Date: Aug. 10, 2018

(87) PCT Pub. No.: WO2017/137865
PCT Pub. Date: Aug. 17, 2017

(65) Prior Publication Data
US 2019/0076300 A1    Mar. 14, 2019

(30) Foreign Application Priority Data
Feb. 11, 2016    (IT) ..................... 102016000013987

(51) Int. Cl.
*A61F 13/15*    (2006.01)
*A61F 13/49*    (2006.01)

(52) U.S. Cl.
CPC .. *A61F 13/15585* (2013.01); *A61F 13/15723* (2013.01); *A61F 13/15756* (2013.01); *A61F 13/15764* (2013.01); *A61F 13/49007* (2013.01)

(58) Field of Classification Search
CPC .......... A61F 13/15756; A61F 13/15764; A61F 13/49007; A61F 13/15723; A61F 13/15585
See application file for complete search history.

(56) References Cited

U.S. PATENT DOCUMENTS

2004/0245069 A1    12/2004  Hook et al.
2013/0184137 A1*   7/2013   Umebayashi ........... A61F 13/15
                                                        493/343

FOREIGN PATENT DOCUMENTS

EP    2172171 A1    4/2010
EP    2238955 A1   10/2010
WO    WO2014076626 A1  5/2014

OTHER PUBLICATIONS

International Search Report and Written Opinion dated May 11, 2017 for counterpart PCT Application No. PCT/IB2017/050476.

* cited by examiner

*Primary Examiner* — Vishal I Patel
(74) *Attorney, Agent, or Firm* — Shuttleworth & Ingersoll, PLC; Timothy Klima

(57) ABSTRACT

A method for making absorbent sanitary articles whereby each absorbent article is provided with at least one pair of side tabs. The method includes the steps of feeding a single continuous web with a longitudinal axis towards at least one cutting station where the continuous web is divided, by a succession of cuts transverse to the longitudinal axis, into a first and a second series of side tabs, each of which has an asymmetrical shape and separately applying each rotated side tab of the first series and each side tab of the second series along a continuous strip of a material for making the absorbent articles, in such a way that each rotated tab of the first series is juxtaposed with a respective tab of the second series to define a respective pair of side tabs.

11 Claims, 5 Drawing Sheets

METHOD AND A MACHINE FOR MAKING ABSORBENT SANITARY ARTICLES

This application is the National Phase of International Application PCT/IB2017/050476 filed Jan. 30, 2017 which designated the U.S.

This application claims priority to Italian Patent Application No. 102016000013987 filed Feb. 11, 2016, which application is incorporated by reference herein.

TECHNICAL FIELD

This invention relates to a method and a machine for making absorbent sanitary articles.

More specifically, the invention relates to a method and a machine for making absorbent sanitary articles such as disposable nappies for children or adults.

BACKGROUND ART

As is known, these articles are obtained by laying a sheet of impermeable material over a sheet of permeable material (of non-woven fabric) and interposing an absorbent pad between the two sheets.

The absorbent article also comprise further accessory components, such as side tabs for fastening the nappy round the wearer's waist.

Generally, a prior art machine of this kind comprises a feed line for advancing a continuous strip of material for making the absorbent articles and which is subsequently cut into the individual absorbent articles.

More specifically, the side tabs are applied to the continuous strip along predetermined stretches so that when the strip is cut, each absorbent article has at least one pair of side tabs.

DISCLOSURE OF THE INVENTION

In this context, the need for a method and a machine for making absorbent sanitary articles is felt.

In particular, the absorbent sanitary articles have an asymmetrical shape, preferably trapezoidal.

BRIEF DESCRIPTION OF THE DRAWINGS

Further features and advantages of this invention are more apparent in the description below, with reference to a preferred, non-limiting embodiment of a machine for making absorbent sanitary articles as illustrated in the accompanying drawings, in which.

DETAILED DESCRIPTION OF PREFERRED EMBODIMENTS OF THE INVENTION

Figure 1:
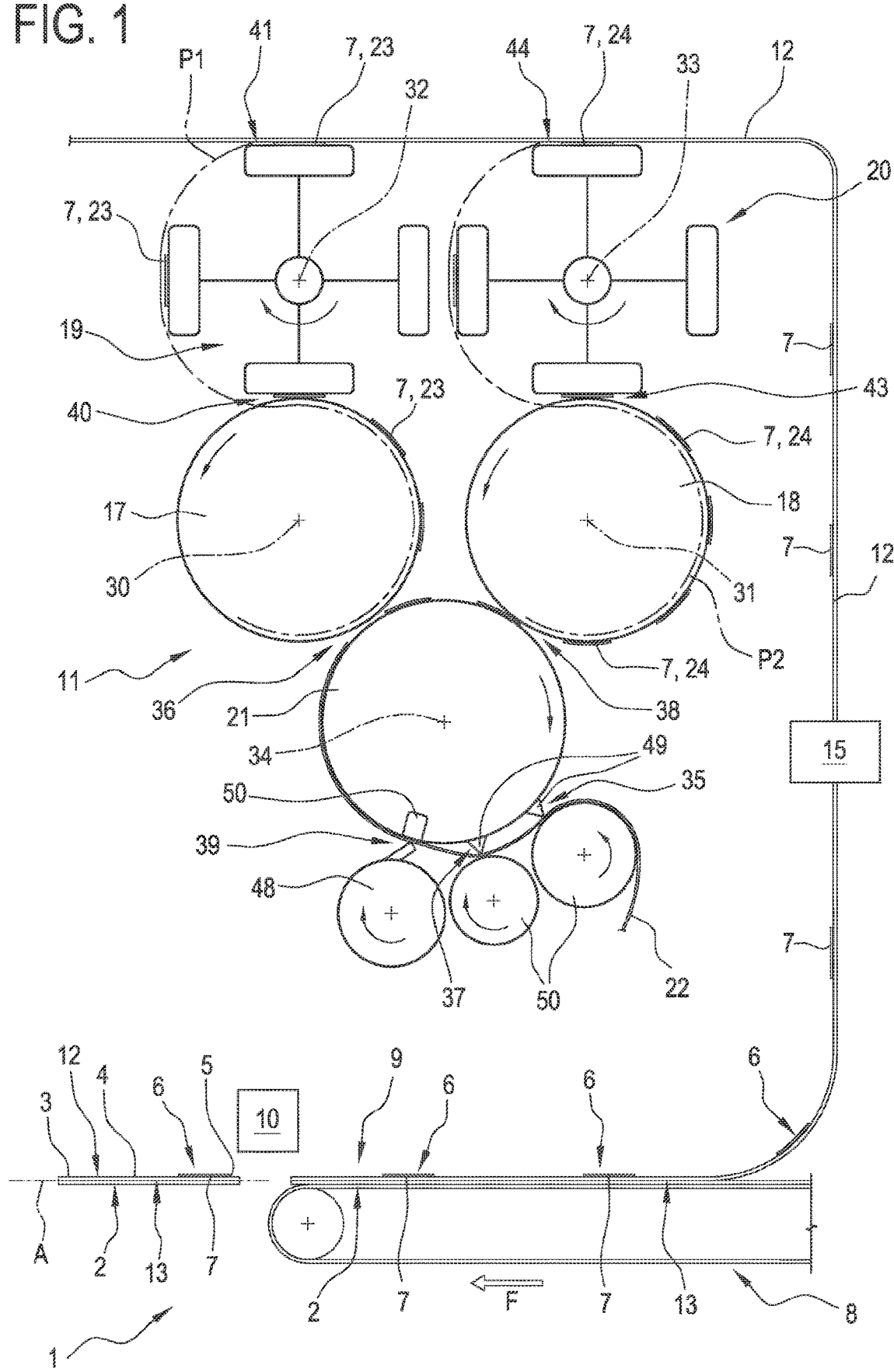
FIG. 1 is a schematic front view illustrating a machine for making absorbent sanitary articles according to this invention.

With reference to FIG. 1, the numeral 1 denotes in its entirety a machine for making absorbent sanitary articles 2.

The absorbent sanitary article 2 has a substantially rectangular shape extending along a longitudinal axis A and comprises, in a line along the axis A, a front portion 3, a central portion 4 and a rear portion 5.

The absorbent article 2 comprises a sheet of permeable material 12, in particular non-woven fabric, and a sheet of impermeable material 13, in particular polyethylene.

An inner absorbent pad, not illustrated, is sandwiched between the sheet of permeable material 12 and the sheet of impermeable material 13.

The absorbent article 2 comprises at least one pair 6 of side tabs 7 which project from the rear portion 5 transversely to the axis A.

The side tabs 7 are, in use, designed to be placed over respective fastening zones of the front portion 3 in order to close the absorbent article 2 round the wearer's waist.

Preferably, the side tabs 7 comprise fastening means 14 to guarantee their fastening to the front portion 3 of the absorbent article 2. Preferably, the side tabs 7 are made of elastic material.

The machine 1 comprises a feed line 8 for advancing a continuous strip 9 of material for making the absorbent articles 2.

A cutting means 10 divides the continuous strip 9 into the individual absorbent articles 2.

The continuous strip 9 advances along the feed line 8 in a feed direction D as indicated in FIG. 1 by the arrow F.

The machine 1 comprises a unit 11 for forming and applying at least one pair 6 of side tabs 7.

According to the invention, the side tabs 7 are applied to the sheet of permeable material 12.

Figure 4:
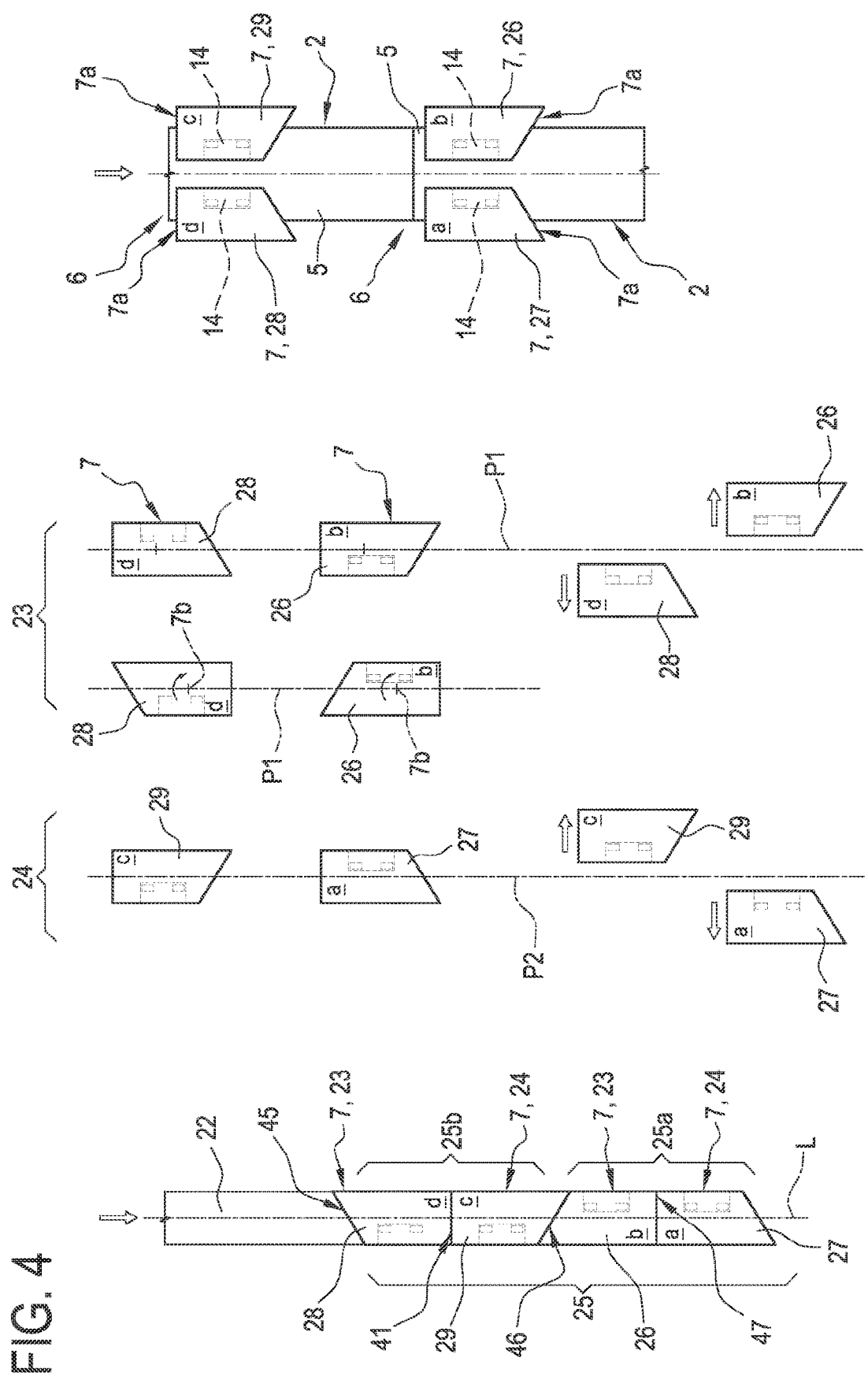
FIG. 4 schematically illustrates the steps in the making of the side tabs in the machine of FIG. 1, without waste.
Figure 5:
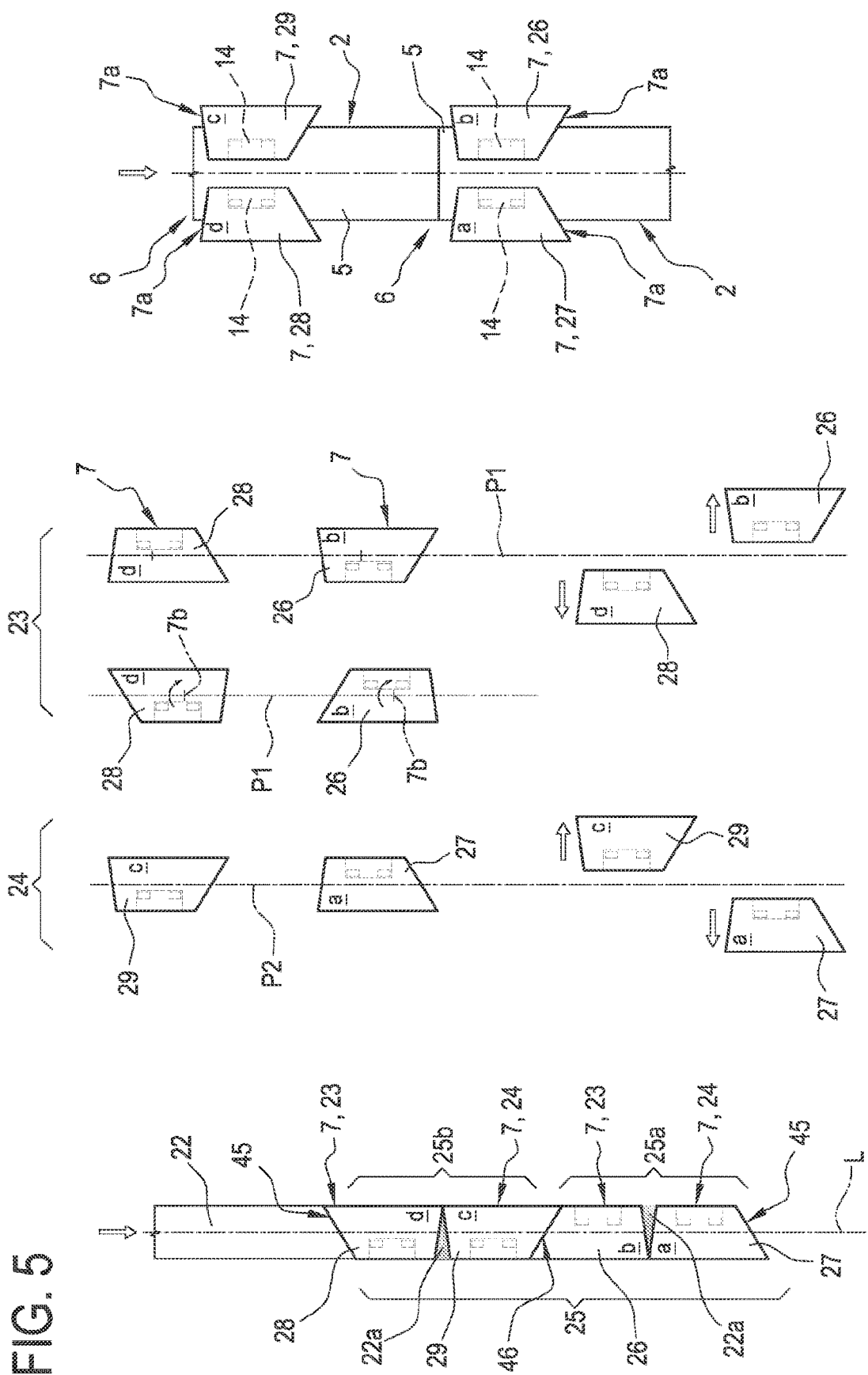
FIG. 5 schematically illustrates the steps in the making of the side tabs in the machine of FIG. 1, with waste.

More specifically, each side tab 7 is applied to the sheet of permeable material 12 in such a way that a portion 7a of the side tab protrudes from the sheet of permeable material 12, as shown in FIGS. 4 and 5.

Folding means 15, located downstream of the unit 11 for forming and applying the pair 6 of side tabs 7 in the feed direction of the sheet of permeable material 12, engage the protruding portions 7a of the side tabs 7 and fold them onto the sheet of permeable material 12.

In a first variant, the folding means 15 fold the portion 7a towards the inside of the sheet of permeable material 12 in such a way as to interpose it between the sheet of permeable material 12 and the sheet of impermeable material 13.

The sheet of permeable material 12 with the folded portions 7a of the side tabs 7 is coupled to the sheet of impermeable material 13 in such a way that the portions 7a are sandwiched between the sheet of permeable material 12 and the sheet of impermeable material 13.

Adhesive fastening means, not illustrated, securely connect the portions 7a of the side tabs 7 to the sheet of permeable material 12 and/or to the sheet of impermeable material 13.

In a second variant, the folding means 15 fold the portion 7a of the side tabs 7 onto the sheet of permeable material 12, in particular onto the side of the permeable material 12 which is accessible to the user when the absorbent article 2 is being used.

The forming and application unit 11 comprises a plurality of conveyors 17, 18, 19, 20, 21 which rotate about respective axes 30, 31, 32, 33, 34 which are all parallel to a transverse direction, relative to the feed direction D of the continuous strip 9.

More specifically, the forming and application unit 11 comprises a conveyor roller 21 for transporting a single continuous web 22 with a longitudinal axis L.

The conveyor roller 21 rotates about a respective main axis of rotation 34.

The conveyor roller 21 feeds the continuous web 22 towards at least one cutting station 35, 37, 39 to make on the continuous web 22 a succession of cuts transverse to its longitudinal axis L, in particular subdividing the continuous web 22 into a first and a second series 23 and 24 of side tabs 7.

The side tabs 7 of the first and second series 23 and 24 are arranged alternately with each other in a continuous succession 25.

The continuous web 22 is subdivided in such a way that each side tab 7 of the first series 23 is alternated with a side tab 7 of the second series 24.

In the one or more cutting stations 35, 37, 39, the continuous web 22 is subdivided into at least four side tabs 7 defining the continuous succession 25.

In other words, the continuous web 22 is subdivided into a plurality of continuous successions 25 which follow each other.

The continuous succession 25 comprises, in the following order, a first side tab 27 of the second series 24, a first side tab 26 of the first series 23, a second side tab 29 of the second series 24 and a second side tab 28 of the first series 23, as illustrated in FIGS. 4 and 5.

The first series 23 is defined by the alternating succession of the first and second side tabs 26 and 28.

The second series 24 is defined by the alternating succession of the first and second side tabs 27 and 29.

According to this invention, each of the four side tabs 7 of the succession 25 is oriented differently to the other with reference to the position plane of the side tab 7 itself.

More specifically, the first side tab 26 of the first series 23 is oriented differently to the second side tab 28 of the first series 23 with reference to the position plane of each side tab 26 and 28 itself.

The first side tab 27 of the second series 24 is oriented differently to the second side tab 29 of the second series 24 with reference to the position plane of each side tab 27 and 29 itself.

The first side tab 26 of the first series 23, the first side tab 27 of the second series 24, the second side tab 28 of the first series 23 and the second side tab 29 of the second series 24 are oriented differently to each other with reference to the position plane of each side tab 26, 27, 28 and 29 itself.

Generally speaking, the continuous succession 25 comprises a succession of pairs 25a and 25b of the side tabs 7 which are mirror-symmetrical about an axis which is at right angles to the longitudinal axis L of the web 22.

More specifically, the continuous succession 25 comprises a pair 25a, defined by a first tab 26 of the first series 23 and a first tab 27 of the second series 24 which are consecutive and mirror-symmetrical to each other, and a pair 25b, defined by a second tab 28 of the first series 23 and a second tab 29 of the second series 24 which are consecutive and mirror-symmetrical to each other.

Moreover, it should be noted that the pair 25a defined by the side tabs 26 and 27 of the first and second series 23 and 24 is mirror-symmetrical with respect to the pair 25b defined by the side tabs 27 and 29 of the first and second series 23 and 24 about an axis which is parallel to the longitudinal axis of the continuous web 22.

The continuous web 22 is subdivided into the continuous succession 25 of pairs 25a and 25b arranged alternately with each other.

A first means 17 for picking up individual side tabs 7 of the first series 23, in particular the first and second side tabs 26 and 28 of the first series 23 is located downstream of the conveyor roller 21.

More specifically, the first pickup means 17 is tangent to the conveyor roller 21 at a respective first pickup station 36.

Preferably, the first pickup means 17 is in the form of a roller 17 which rotates about a respective main axis of rotation 30.

A first means 19 for transferring individual side tabs 7 of the first series 23, in particular the first and second side tabs 26 and 28 of the first series 23 is located downstream of the first pickup means 17.

The first transfer means 19 is tangent to the first pickup means 17 at a respective transit station 40.

Preferably, the first transfer means 19 is rotatable about a respective main axis of rotation 32.

The first transfer means 19 conveys and applies each side tab 7 of the first series 23, in particular each first and second side tab 26 and 28 of the first series 23 to the continuous strip 9, in particular at an application station 41.

In other words, the side tabs 7 of the first series 23, in particular each first and second side tab 26 and 28 of the first series 23, follow a first path P1, which in particular extends from a respective pickup station 36 to a respective application station 41.

According to the invention, along the first path P1, each side tab 7 of the first series 23 is rotated by 180° about a respective axis of rotation 7b perpendicular to the plane containing the side tab 7 itself.

More specifically, along the first path P1, the first and second side tabs 26 and 28 of the first series 23 are each rotated by 180° about the respective axis of rotation 7b perpendicular to the plane containing the side tab 7 itself.

The rotation by 180° about the axis of rotation 7b is clockwise.

The side tabs 7 of the first series 23, in particular the first and second side tabs 26 and 28, are each rotated by 180° while being transfer by the first pickup means 17, in particular from the first pickup station 36 to the corresponding transit station 40.

More precisely, relative to the axis of rotation 30 of the first pickup means 17, the axis of rotation 7b of the side tabs 7 is disposed along a substantially radial direction.

The first pickup means 17 comprises a plurality of pads, not illustrated, disposed along its outside surface, each of which is intended to receive a respective side tab 7 of the first series 23. The pads, not illustrated, are positioned one after the other in a single succession.

Each pad, not illustrated, is rotatable about a respective axis of rotation perpendicular to the respective surface containing the side tab 7.

According to the invention, along the first path P1, each side tab 7 of the first series 23, in particular each first and second side tab 26 and 28, is translated sideways from a starting position, in particular corresponding to the position adopted at the first pickup station 36, to an end position, in particular adopted at the first application station 41.

This sideways translation is performed in a direction parallel to the direction of the axes of rotation of the conveyors 17 and 19 disposed along the first path P1, in particular the first pickup means 17 and the first transfer means 19.

Preferably, each side tab 7 of the first series 23, in particular each first and second side tab 26 and 28, is translated sideways from the starting position to the end position after being rotated by 180° about the respective axis 7b.

Preferably, each side tab 7 of the first series 23, in particular each first and second side tab 26 and 28, is translated sideways from the starting position to the end position while being transferred by the first transfer means 19, in particular from the transit station 40 to the corresponding first application station 41.

Alternatively, the translation of each side tab 7 of the first series 23, in particular each first and second side tab 26 and 28 from the starting position to the end position is performed at least partly as a result of the respective 180° rotation, in particular while being transferred by the first pickup means 17.

According to the invention, the side tabs 7 of the first series 23 are translated sideways from the starting position to the end position reciprocatingly in a first and a second positioning direction, opposite to each other, in such a way that the first side tab 26 is applied on the left of the continuous strip 9 and the second side tab 28 is applied, consecutively to the first side tab 26, on the right of the continuous strip 9.

The term "right" means the side of the continuous strip 9 directed towards the part of the machine 1 accessible to the operator.

The term "left" means the side of the continuous strip 9 directed towards the inside of the machine 1 not accessible to the operator.

A second means 18 for picking up individual side tabs 7 of the second series 24, in particular the first and second side tabs 27 and 29 of the second series 24 is positioned tangent to the conveyor roller 21, at a respective second pickup station 38, downstream of the first means 17 for picking up the side tabs 7 of the first series 23.

More specifically, the second pickup means 18 is in the form of a roller 18 which rotates about a respective main axis of rotation 31.

A second means 20 for transferring individual side tabs 7 of the second series 24 is located downstream of the second pickup means 18.

The second transfer means 20 is rotatable about a respective main axis of rotation 33.

More specifically, the second transfer means 20 is tangent to the second pickup means 18 at a respective transit station 43.

The second transfer means 20 conveys and applies each side tab 7 of the second series 24, in particular each first and second side tab 27 and 29 of the second series 24 to the continuous strip 9, in particular at a second application station 44.

In other words, the side tabs 7 of the second series 24, in particular each first and second side tab 27 and 29 of the second series 24, follow a second path P2, which extends from a respective pickup station 38, in particular the second pickup station 38, to a respective application station 44 on the continuous strip 9, in particular a second application station 44.

The second path P2 is distinct from the first path P1.

Along the second path P2, each side tab 7 of the second series 24, in particular each first and second side tab 27 and 29, keeps unchanged a respective orientation, relative to an axis of rotation 7b perpendicular to the plane containing the side tab itself, in particular the orientation corresponding to the position adopted at the respective pickup station 38.

It should be noted that the orientation adopted by each first and second side tab 27 and 29 of the second series 24 is defined by the mode of cutting the continuous web 22, as described below.

The second pickup means 18 comprises a plurality of pads, not illustrated, disposed along its outside surface, each of which is intended to receive a respective side tab 7 of the second series 24.

The pads, not illustrated, are positioned one after the other in a single succession.

Each pad, not illustrated, of the second pickup means 18 is rotatable about a respective axis of rotation perpendicular to the respective surface containing the side tab 7.

According to the invention, along the second path P2, each side tab 7 of the second series 24, in particular each first and second side tab 27 and 29, is translated sideways from a starting position, in particular corresponding to the position adopted at the second pickup station 38, to an end position, in particular adopted at the second application station 44.

This sideways translation is performed in a direction parallel to the direction of the axes of rotation of the conveyors 18 and 20 disposed along the second path P2, in particular of the second pickup means 18 and of the second transfer means 20.

Preferably, each side tab 7 of the second series 24, in particular each first and second side tab 27 and 29, is translated sideways from the starting position to the end position while being transferred by the second transfer means 20, in particular from the transit station 43 to the corresponding application station 44.

According to the invention, the side tabs 7 of the second series 24 are translated from the starting position to the end position reciprocatingly in opposite first and a second positioning directions, in such a way that each first side tab 27 of the second series 24 is applied on the right of the continuous strip 9 and the second side tab 29 is applied, consecutively to the first side tab 27, on the left of the continuous strip 9.

It should be noted that as described herein and according to the invention, each side tab 7 of the first series 23 and each rotated side tab 7 of the second series are applied separately along the continuous strip 9, in such a way that each side tab 7 of the first series 23 is juxtaposed with a respective tab 7 of the second series 24 to define a pair 6 of side tabs 7.

The sideways translation of the side tabs 7 of the first and second series 23 and 24 intended to define a respective pair 6 allows them to be positioned on the continuous strip 9 so as to define a predetermined final mutual distance d from the waistline of the absorbent article 2.

Each side tab 7 of the first series 23, in particular each first and second side tab 26 and 28, is applied to the continuous strip 9 according to a predetermined spacing P so that each side tab 7 of the first series 23 will become part of a respective absorbent article 2.

In other words, each first side tab 26 of the first series 23 applied to the continuous strip 9 is spaced from the second side tab 28 of the first series 23 consecutive to it so that the first side tab 26 and the second side tab 28 will become part of a respective absorbent article 2.

Each side tab 7 of the first series 23 is spaced at the spacing P while being transferred by the first transfer means 19, in particular from the transit station 40 to the corresponding first application station 41.

According to the invention, each side tab 7 of the first series 23, in particular each first and second side tab 26 and 28, is translated sideways from the starting position to the end position and simultaneously spaced at the predetermined spacing P, in particular while being transferred by the first transfer means 19.

Each side tab 7 of the second series 24, in particular each first and second side tab 27 and 29, is applied to the continuous strip 9 according to a predetermined spacing P so that each side tab 7 of the second series 24 will become part of a respective absorbent article 2.

In other words, each first side tab 27 of the first series 24 applied to the continuous strip 9 is spaced from the second side tab 29 of the second series 24 consecutive to it so that the first side tab 27 and the second side tab 29 will become part of a respective absorbent article 2.

Each side tab 7 of the second series 24 is spaced at the spacing P while being transferred by the second transfer means 20, in particular from the transit station 43 to the corresponding second application station 44.

According to the invention, each side tab 7 of the second series 24, in particular each first and second side tab 27 and 29, is translated sideways from the starting position to the end position and simultaneously spaced at the predetermined spacing P, in particular while being transferred by the second transfer means 20.

According to the invention, each first and second side tab 26 and 28 of the first series 23 alternately defines the right-hand side tab 7 and the left-hand side tab 7 of respective absorbent articles 2 which are consecutive to each other along the continuous strip 9.

According to the invention, each first and second side tab 27 and 29 of the second series 24 alternately defines the left-hand side tab 7 and the right-hand side tab 7 of respective absorbent articles 2 which are consecutive to each other along the continuous strip 9.

According to the invention, each first side tab 26 of the first series 23 defines a pair 6 with a respective first side tab 27 of the second series 24.

According to the invention, each second side tab 28 of the first series 23 defines a pair 6 with a respective second side tab 29 of the second series 24.

With reference to the continuous strip 9, the pairs 6 defined by the first side tabs 26 and 27 of the first and second series 23 and 24 are alternated in succession with the pairs 6 defined by the second side tabs 28 and 29 of the first and second series 23 and 24.

It should be noted that the method described, from cutting the continuous web 22 to applying the side tabs 7, is schematically illustrated in FIGS. 4 and 5.

Figure 2:
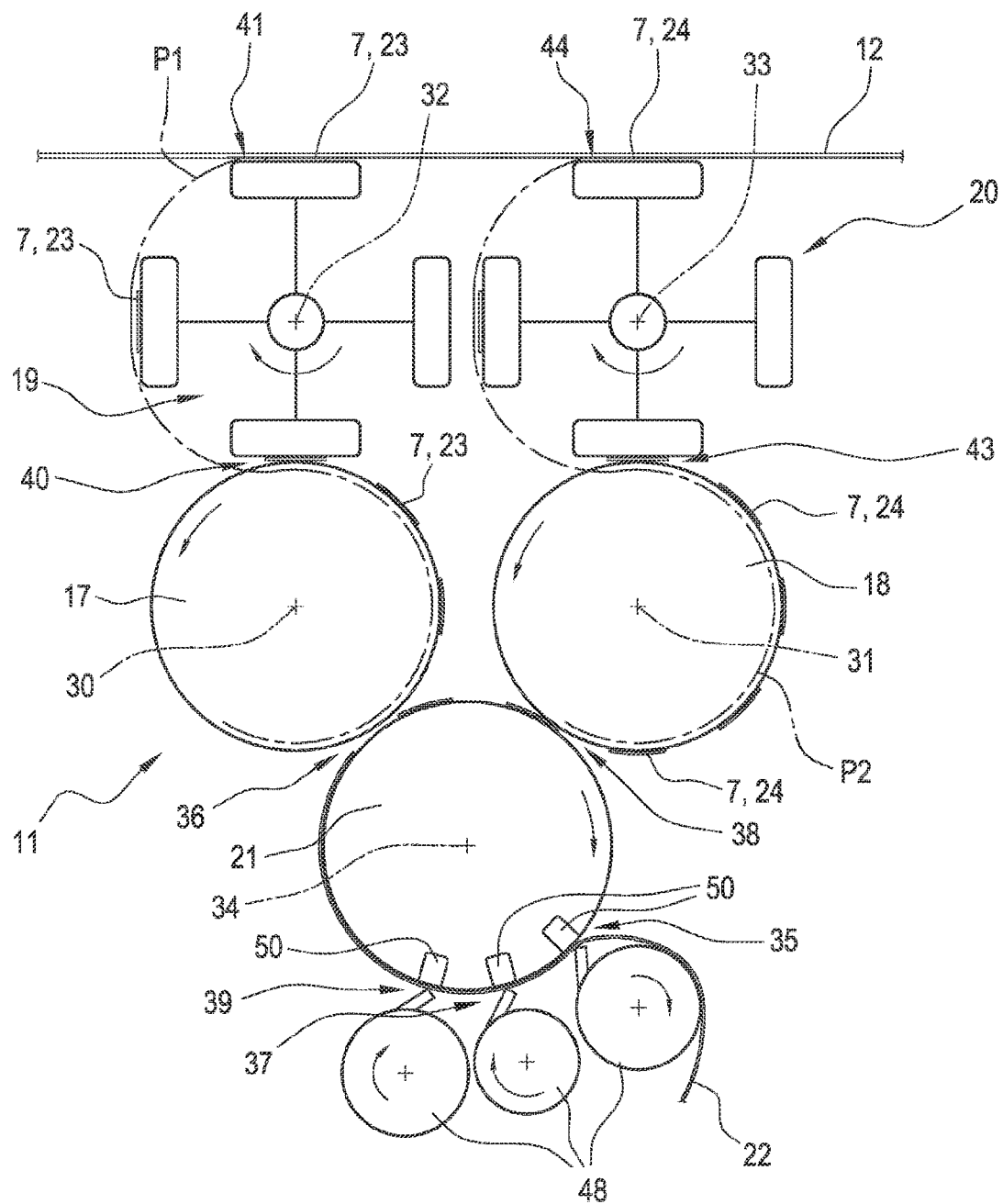
FIG. 2 shows a first variant of the machine of FIG. 1.
Figure 3:
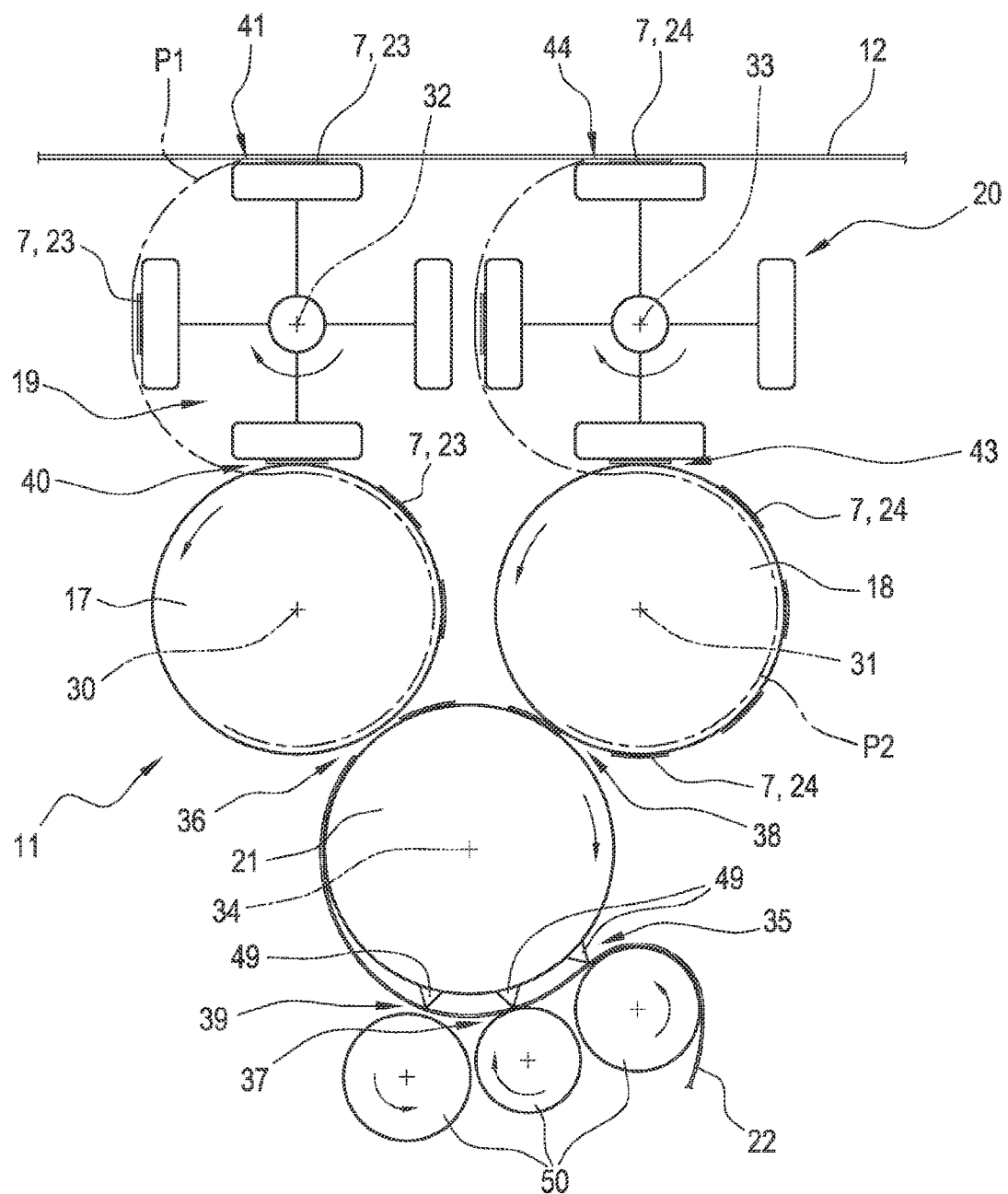
FIG. 3 shows a second variant of the machine of FIG. 1.

With reference in particular to cutting the continuous web 22, as illustrated in FIGS. 1 to 3, the web is fed towards a first cutting station 35 and a second cutting station 37, which are distinct from each other.

At the first cutting station 35, at least a first cut 45, inclined to the longitudinal axis L of the web 22, is made on the continuous web 22.

At the second cutting station 37, at least a second cut 46, which is inclined along a direction transverse to the longitudinal axis L of the web 22 and whose orientation is distinct from that of the first cut 45, is made on the web 22.

More specifically, the first and second cuts 45 and 46 are mirror-symmetrical to each other.

In a first variant, the continuous web 22 is fed to a third cutting station 39, where a third cut 47 is made on the continuous web 22, at right angles to the longitudinal axis L of the web 22, as illustrated in FIG. 4.

Considering the succession of cuts made on the continuous web 22, the third cut 47 is interposed between the first and the second cut 45 and 46.

In a second variant, the continuous web 22 is fed to a third cutting station 39, where a portion 22a of the continuous web 22 corresponding in shape to the profile of the cutting means 49 is removed, as illustrated in FIG. 5.

In this embodiment, the portion 22a of the continuous web 22 has the shape of a triangle, in particular an isosceles triangle, whose base coincides with one of the sides of the web 22 and whose equal sides are transverse to the longitudinal axis L of the web 22.

Removing the portion 22a of the continuous web 22 produces a variant of the third cut 47 at right angles to the longitudinal axis L of the web 22.

Considering the succession of cuts made on the continuous web 22, the portion 22a removed from the web 22 is interposed between the first and the second cut 45 and 46.

More specifically, considering the succession of cuts made on the continuous web 22, the portions 22a of the continuous web 22 are alternately rotated by 180°.

In the variants illustrated in FIGS. 1 to 3, it should be considered that in order to make the cut 47 at right angles to the longitudinal axis L of the web 22, called third cut 47, a cutting means 48 is disposed to face and be tangent to the outside surface of the conveyor roller 21.

In this variant, part of the outside surface of the conveyor roller 21, acts as an anvil 50.

The anvil 50 and the cutting means 48 define the respective cutting station 39, in particular the third cutting station 39.

In order to make the cuts 45 and 46, which are inclined to the longitudinal axis L of the web 22 and which are called first and second cuts 45 and 46, or to remove a portion 22a of the continuous web 22, the unit 11 comprises respective cutting means 49 disposed on the outside surface of the conveyor roller 21.

In this variant, for each cutting means 49, there is a respective anvil 50 disposed to face and be tangent to the outside surface of the conveyor roller 21 in such a way as to cut the web 22 in the required zone.

The anvils 50 are preferably in the form of rollers which are rotatable about respective main axes 50a.

Depending on the shape of the side tabs 7 of the succession 25 to be made along the continuous web 22, the conveying roller 21 comprises one or more cutting means 49 distributed along the outside surface of the roller 21 and/or one or more portions 50 defining an anvil 50 of a respective cutting means 48, facing the outside surface of the conveying roller 21 and acting in conjunction therewith.

With reference to FIG. 1, the conveyor roller 21 comprises at least one outside surface portion defining an anvil 50 of a respective cutting means 48 facing it and acting in conjunction therewith, in particular for making the cut 47 at right angles to the longitudinal axis L of the web 22, and at least two cutting means 49 distributed along the outside surface of the roller 21, in particular for making the cuts 45 and 46 inclined to the longitudinal axis L of the web 22 and each having a distinct orientation. For each cutting means 49, there is a respective anvil 50 acting in conjunction therewith and disposed to face and be tangent to the outside surface of the conveyor roller 21.

With reference to FIG. 3, the conveyor roller 21 comprises at least three outside surface portions, each defining an anvil 50 of a respective cutting means 48 facing it and acting in conjunction therewith, in particular for making the cut 47 at right angles to the longitudinal axis L of the web 22, and for making the cuts 45 and 46 inclined to the longitudinal axis L of the web 22 and each having a distinct orientation.

With reference to FIG. 2, the conveyor roller 21 comprises at least three cutting means 49 distributed along the outside surface of the roller 21, in particular for making the cuts 45 and 46 inclined to the longitudinal axis L of the web 22, each having a distinct orientation, and for removing a portion 22a from the web 22. For each cutting means 49, there is a respective anvil 50, in particular in the form of a roller 50, disposed to face and be tangent to the outside surface of the conveyor roller 21 and acting in conjunction with a respective cutting means 49.

Advantageously, whenever the shape of the side tabs 7 of the succession 25 to be made along the continuous web 22 needs to changed, the conveyor roller 21 and any cutting means 48, 49 and/or anvils 50 acting in conjunction therewith must be substituted.

Advantageously, the unit for forming and applying the side tabs 7 is more efficient than prior art machines and thus increases the productivity of the machine 1.

Lastly, it should be noted that the machine 1 according to this invention comprises a unit 11 for forming and applying pairs 6 of side tabs 7 arranged in a trailing portion 5 and a unit 11 for forming and applying pairs 6 of side tabs 7 arranged in a leading portion 3 of an absorbent article 2.

In this embodiment, respective pairs 6 of side tabs 7 of the trailing portion 5 of the absorbent article 2 are obtained from a single continuous web 22 and respective pairs 6 of side tabs 7 of the leading portion 4 of the absorbent article 2 are obtained from a single continuous web 22.

The invention claimed is:

1. A method for making sanitary absorbent articles whereby each absorbent article is provided with a pair of side tabs, the method comprising:
    feeding a continuous web, with a longitudinal axis, towards a cutting station where the continuous web is subdivided by a succession of cuts transverse to the longitudinal axis into a first and a second series of side tabs, each of which has an asymmetrical shape; the side tabs of the first and the second series being arranged alternately with each other in a continuous succession;
    subdividing the continuous web according to a continuous repetition of the continuous succession, each of which comprises a succession of pairs of side tabs which are mirror-symmetrical to each other along respective axes at right angles to the longitudinal axis of the continuous web; each continuous succession comprising a pair defined by a first tab of the first series and a first tab of the second series which are consecutive and mirror-symmetrical to each other along a first axis at right angles to the longitudinal axis of the continuous web, and a pair defined by a second tab of the first series and a second tab of the second series which are consecutive and mirror-symmetrical to each other along a second axis at right angles to the longitudinal axis of the continuous web;
    separating the side tabs of the first series from the continuous web and feeding the side tabs of the first series along a first path along which each side tab is rotated by 180° about an axis of rotation perpendicular to a plane containing the side tab;
    separating the side tabs of the second series from the continuous web and feeding the side tabs of the second along a second path, distinct from the first path and along which each side tab keeps unchanged its respective orientation relative to the plane containing the side tab;
    applying each rotated side tab of the first series and each side tab of the second series along a continuous strip of a material for making the absorbent articles, in such a way that each rotated side tab of the first series is juxtaposed with a respective side tab of the second series to define a respective pair of side tabs;
    along the first path, translating each side tab of the first series sideways relative to an initial pickup position until reaching a final position of application on the continuous strip so as to define alternately a left-hand side tab and a right-hand side tab of a respective pair of side tabs of respective absorbent articles which are consecutive to each other along the continuous strip;
    along the second path, translating each side tab of the second series sideways relative to an initial pickup position until reaching a final position of application on the continuous strip so as to define alternately a further right-hand side tab and a further left-hand side tab of a respective pair of side tabs of respective absorbent articles which are consecutive to each other along the continuous strip.

2. The method according to claim 1, and further comprising applying each rotated side tab of the first series and each side tab of the second series separately along the continuous strip.

3. The method according to claim 1, and further comprising performing the step of translating the side tab of the first series sideways along the first path from the initial position to the final position after the step of rotating the side tab by 180° about the respective axis of rotation perpendicular to the plane containing the side tab.

4. The method according to claim 1, and further comprising a step of arranging along the first path each side tab of the first series according to a predetermined spacing and arranging along the second path each side tab of the second series according to a predetermined spacing in such a way that each side tab of the first and the second series becomes part of a respective absorbent article.

5. The method according to claim 4, and further comprising performing the step of translating each side tab of the first series sideways simultaneously with the step of arranging according to the predetermined spacing each side tab of the first series; and performing the step of translating each side tab of the second series sideways simultaneously with the step of arranging according to the predetermined spacing each side tab of the second series.

6. The method according to claim 1, wherein the continuous repetition of the continuous succession includes four side tabs defined by a first and a second side tab of the first series arranged alternately with a first and a second side tab of the second series; each of the four side tabs of the continuous succession being oriented differently from the others of the four side tabs.

7. The method according to claim 1, wherein the feeding a continuous web comprises feeding a first continuous web from which respective pairs of side tabs of a trailing portion of the absorbent article are obtained and feeding a second continuous web from which respective pairs of side tabs of the leading portion of the absorbent article are obtained.

8. A machine for making sanitary absorbent articles, comprising:
    a feed line for feeding a continuous strip of a material for making the absorbent articles,
    a cutting unit for cutting the continuous strip into individual absorbent articles,
    a forming and application unit for forming and applying a pair of side tabs to the absorbent articles;
    the forming and application unit comprising a plurality of conveyors which rotate about respective axes which are all parallel to a transverse direction, relative to a feed direction of the continuous strip, and which comprise:
        a conveying roller for conveying a single continuous web with a longitudinal axis towards at least one cutting station and for making on the continuous web a succession of cuts to the longitudinal axis to divide the continuous web into a first and a second series of side tabs, each of which has an asymmetrical shape; the side tabs of the first and the second series being arranged alternately with each other in a continuous succession;

the forming and application unit configured to subdivide the continuous web according to a continuous repetition of a continuous succession, each of which comprises a succession of pairs of side tabs which are mirror-symmetrical to each other along respective axes at right angles to the longitudinal axis of the continuous web; each continuous succession comprising a pair defined by a first tab of the first series and a first tab of the second series which are consecutive and mirror-symmetrical to each other along a first axis at right angles to the longitudinal axis of the continuous web, and a pair defined by a second tab of the first series and a second tab of the second series which are consecutive and mirror-symmetrical to each other along a second axis at right angles to the longitudinal axis of the continuous web;

a first and a second pickup unit for picking up the side tabs of the first and the second series, respectively, at a first and a second pickup station, both located downstream of the at least one cutting station; the first pickup unit rotating each side tab by 180° about an axis of rotation perpendicular to a plane containing the side tab; the second pickup unit keeping unchanged a respective orientation of each side tab relative to an axis of rotation perpendicular to the plane containing the side tab;

a first transfer unit for transferring each side tab of the first series positioned downstream of the first pickup unit to convey and apply each rotated side tab of the first series to the continuous strip;

a second transfer unit for transferring each side tab of the second series and positioned downstream of the second pickup unit to convey and apply each side tab of the second series to the continuous strip in such a way that each rotated tab of the first series is juxtaposed with a respective tab of the second series to define a respective pair of side tabs;

the first transfer unit configured to translate each side tab of the first series sideways relative to an initial pickup position until reaching a final position of application on the continuous strip so as to define alternately a left-hand side tab and a right-hand side tab of a respective pair of side tabs of respective ones of the absorbent articles which are consecutive to each other along the continuous strip;

the second transfer unit configured to translate each side tab of the second series sideways relative to an initial pickup position until reaching a final position of application on the continuous strip so as to define alternately a further right-hand side tab and a further left-hand side tab of a respective pair of side tabs of the respective ones of the absorbent articles which are consecutive to each other along the continuous strip.

9. The machine according to claim 8, wherein the first transfer unit is configured to arrange each side tab of the first series according to a predetermined spacing and in the second transfer unit is configured to arrange each side tab of the second series according to a predetermined spacing in such a way that each side tab of the first and the second series becomes part of a respective one of the absorbent articles.

10. The machine according to claim 8, and further comprising at least one chosen from the at least one cutting station being distributed along an outside surface of the conveying roller and an anvil of the at least one cutting station facing the outside surface of the conveying roller and acting in conjunction therewith.

11. The machine according to claim 8, wherein the forming and application unit includes a first sub-unit for forming and applying pairs of side tabs arranged in a trailing portion of a respective one of the absorbent articles and a second sub-unit for forming and applying pairs of side tabs arranged in a leading portion of the respective one of the absorbent articles.

* * * * *